United States Patent
Kamikawa et al.

(10) Patent No.: US 6,965,037 B2
(45) Date of Patent: Nov. 15, 2005

(54) METHOD FOR PRODUCING AMINOCARBAZOLES

(75) Inventors: Takashi Kamikawa, Nara (JP); Osamu Maruyama, Oita (JP)

(73) Assignee: Sumitomo Chemical Company, Limited, Osaka (JP)

(*) Notice: Subject to any disclaimer, the term of this patent is extended or adjusted under 35 U.S.C. 154(b) by 225 days.

(21) Appl. No.: 10/199,028

(22) Filed: Jul. 22, 2002

(65) Prior Publication Data

US 2002/0183526 A1 Dec. 5, 2002

Related U.S. Application Data

(63) Continuation of application No. 09/455,506, filed on Dec. 6, 1999, now abandoned.

(30) Foreign Application Priority Data

Dec. 7, 1998 (JP) ............................................ 10-346922
Jan. 5, 1999 (JP) ............................................ 11-000430

(51) Int. Cl.$^7$ ............................................ C07D 209/82
(52) U.S. Cl. ...................................................... 548/440
(58) Field of Search .......................................... 548/440

(56) References Cited

FOREIGN PATENT DOCUMENTS

| JP | 58140070 | 8/1983 |
| JP | 60163863 | 8/1985 |
| JP | 0331708 | 5/1991 |
| JP | 07133261 | 5/1995 |

*Primary Examiner*—Johann Richter
*Assistant Examiner*—Ebenezer Sackey
(74) *Attorney, Agent, or Firm*—Stevens, Davis, Miller & Mosher, L.L.P.

(57) ABSTRACT

Disclosed is a method for producing an aminocarbazole by catalytically reducing a nitrocarbazole, wherein as a catalyst is used an active nickel-based catalyst prepared by contacting a nickel-based catalyst with an alkali and an iron compound under a hydrogen gas or inert gas atmosphere in an inert solvent, and according to the method of the present invention, decrease in reaction speed, decrease in yield of a product or the like depending upon the lot of the starting nitrocarbazoles can be prevented, and aminocarbazoles can be produced in a good yield constantly.

18 Claims, No Drawings

METHOD FOR PRODUCING AMINOCARBAZOLES

CROSS-REFERENCE TO RELATED APPLICATIONS

This application is a continuation application of abandoned U.S. patent application Ser. No. 09/455,506, abandoned, filed Dec. 6, 1999, the entire disclosure of which is incorporated herein by reference.

BACKGROUND OF THE INVENTION

The present invention relates to a method for producing aminocarbazoles. In more detail, the present invention relates to a method for producing aminocarbazoles wherein nitrocarbazoles are catalytically reduced.

Description of the Related Art

Aminocarbazoles are well known compounds as intermediates for dyes, pigments and the like. JP-B-58-140070 discloses a method for producing aminocarbazoles in which a nitrocarbazole is catalytically reduced using a nickel-based catalyst in the presence of an iron compound and an alkali.

However, such a method has caused problems that, in some lots the nitrocarbazole, the raw material caused a decrease in the catalyst activity and the reduction proceeded slowly, and moreover, that the yield of the desired aminocarbazole decreased. These problems may result from the influence of impurities, such as a nitrate, contained in the nitrocarbazole.

SUMMARY OF THE INVENTION

In order to solve the foregoing problems, the present inventors studied extensively on catalysts. As a result, they have found that the use of an active nickel-based catalyst which is prepared by previously contacting a nickel-based catalyst with an alkali and an iron compound under a hydrogen gas or inert gas atmosphere in an inert solvent can prevent the decrease in reaction speed and decrease in yield of the product depending upon the lot of the starting nitrocarbazoles, and that the aminocarbazole can be produced in a good yield constantly. Thus the present invention has been accomplished.

The present invention provides an industrially advantageous method for producing an aminocarbazole by catalytically reducing a nitrocarbazole, wherein an active nickel-based catalyst which is prepared by contacting a nickel-based catalyst with an alkali and an iron compound under a hydrogen gas or inert gas atmosphere in an inert solvent is used as a catalyst.

DESCRIPTION OF THE PREFERRED EMBODIMENTS

The present invention will be described in detail below.

The active nickel-based catalyst used in the present invention is prepared by contacting a nickel-based catalyst with an alkali and an iron compound under a hydrogen gas or inert gas atmosphere in an inert solvent.

Examples of the nickel-based catalyst, which is a raw material of the active nickel-based catalyst, include Raney nickel, stabilized nickel, a nickel catalyst supported on a carrier such as diatomaceous earth, and a nickel catalyst composed mainly of nickel with metals other than nickel such as cobalt, chromium and molybdenum.

Examples of the iron compound include di- or trivalent inorganic iron compounds such as iron(II) oxide, iron(III) oxide, iron(II) hydroxide, iron(III) hydroxide, iron(II) sulfate and iron(III) sulfate. The iron compound is used usually in such an amount that the amount of the iron atoms in the iron compound becomes from 0.1 to 0.6 times by weight as much as the nickel atoms in the nickel-based catalyst.

Examples of the alkali include alkali metal bicarbonates such as sodium hydrogencarbonate and potassium hydrogencarbonate; alkali metal carbonates such as sodium carbonate and potassium carbonate; and alkali metal hydroxides such as sodium hydroxide and potassium hydroxide. These may be used either in the form of an aqueous solution or as it is.

The amount of the alkali used is not particularly limited, but usually is from 0.3 to 1.3% by weight based on the nickel-based catalyst.

The inert solvent is not particular limited as long as it is inert to the nickel-based catalyst and can disperse the nickel-based catalyst well. Examples of such a solvent include water, lower alcohols such as methanol and ethanol, and mixtures of two or more of them. The amount of solvent used is usually from about 5 to 100 times by weight, preferably from about 10 to 50 times by weight based on the total weight of the nickel-based catalyst and the iron compound.

The active nickel-based catalyst used in the present invention is prepared by contacting the above-mentioned nickel-based catalyst with the alkali and the iron compound in the inert solvent under a hydrogen gas or inert gas atmosphere. Example of the method for contacting the nickel based catalyst with the alkali and the iron compound include a method in which a mixture of the nickel-based catalyst, the alkali, the iron compound and the inert solvent is stirred with blowing a hydrogen gas or an inert gas thereinto and a method in which the foregoing mixture is stirred under a hydrogen gas or inert gas atmosphere using a stirring blade.

Examples of the inert gas include nitrogen, argon, helium and the like. The pressure of the hydrogen gas or the inert gas is not particularly limited, but usually is from 0 to 19.6 MPa.-G (gauge pressure), preferably from 0.05 to 9.8 MPa.-G (gauge pressure).

The temperature at which the nickel-based catalyst is contacted with the alkali and the iron compound is not particularly limited, but is usually from about 0 to 200° C., preferably from about 20 to 100° C. The period of time for which the nickel-based catalyst is contacted with the alkali and the iron compound varies depending upon the amounts of the solvent, the nickel-based catalyst and the iron compound and the pressure conditions of the hydrogen gas and the inert gas, and is not limited particularly. It, however, may be determined so as to be sufficient for the nickel-based catalyst to come in contact with the iron compound well.

Thus the active nickel-based catalyst is prepared. The catalyst must be used for the catalytic reduction after isolation from the reaction mixture. However, it is preferred that the resulting catalyst is used for the catalytic reduction as it is, that is without isolating from the reaction mixture.

Examples of the nitrocarbazole, the raw material for the catalytic reduction, include 1-nitrocarbazole, 3-nitrocarbazole, 1-nitro-9-lower alkyl-substituted carbazoles such as 1-nitro-9-methylcarbazole and 1-nitro-9-ethylcarbazole, 3-nitro-9-lower alkyl-substituted carbazole such as 3-nitro-9-methylcarbazole and 3-nitro-9-ethylcarbazole, 3,6-dinitro-9-lower alkyl-substituted carbazoles such as 3,6-dinitro-9-ethylcarbazole, and mixtures of two or more of these nitrocarbazoles.

Such a nitrocarbazole may contain impurities, such as a nitrate, to some extent. For example, a reaction mixture obtained by a post-treatment, such as neutralization, separation and washing with water, of the reaction mixture obtained by nitration of a carbazole in an inert solvent such as chlorinated aromatic solvent can be used directly.

The catalytic reduction is usually carried out in an inert solvent. Examples thereof include chlorinated aromatic solvents such as monochlorobenzene, dichlorobenzene and trichlorobenzene. The amount of the solvent used is usually from about 0.5 to 20 times by weight, preferably from about 1 to 5 times by weight based on the starting nitrocarbazole. It is preferred to make water coexist in order to disperse the active nickel-based catalyst well. It is more preferred that the aforementioned catalyst reaction mixture is used as it is. The catalyst may be added to a mixture of the nitrocarbazole and the solvent. Alternatively, the mixture may be added to the catalyst.

The active nickel-based catalyst is usually used in an amount of from 0.05 to 10% by weight based on the nitrocarbazole in terms of nickel.

The reaction is conducted at a temperature of usually from about 0 to 200° C., preferably from about 30 to 150° C., under a hydrogen pressure of usually from about 0 to 19.6 MPa.-G, preferably from about 0.02 to 9.8 MPa.-G.

After completion of the reaction, an aminocarbazole can be obtained as a solution by carrying out a conventional post-treatment, for example, a post-treatment in which, the catalyst is removed by filtration and an aqueous layer is separated. The aminocarbazole may be isolated as needed.

Examples of the aminocarbazole thus obtained include 1-aminocarbazole, 3-aminocarbazole, 1-amino-9-lower alkyl-substituted carbazoles such as 1-amino-9-methylcarbazole and 1-amino-9-ethylcarbazole-, 3-amino-9-lower alkyl-substituted carbazoles such as 3-amino-9-methylcarbazole and 3-amino-9-ethylcarbazole; 3,6-diamino-9-lower alkyl-substituted carbazoles such as 3,6-diamino-9-ethylcarbazole, and mixtures of two or more of these aminocarbazoles.

According to the method of the present invention, decrease in reaction speed, decrease in yield of a product or the like depending upon the lot of the starting nitrocarbazoles can be prevented, and aminocarbazoles can be produced in a good yield constantly.

EXAMPLES

The following Examples will explain the present invention further in detail, but should not be construed to limit the present invention.

Example 1

Into a stainless steel autoclave equipped with a stirring device, 115 g of water, 1 g of sodium hydroxide, 1.5 g of iron(II) sulfate and 2.2 g of Raney nickel were charged. After replacing the atmosphere in the vessel with hydrogen, the mixture was stirred vigorously at an ordinary temperature for one hour with adjusting the hydrogen pressure to 0.05 MPa.-G to prepare a catalyst.

Into another stainless steel autoclave equipped with a stirring device were charged 110 g of 3-nitro-9-ethylcarbazole (containing 98 ppm of a nitrate), 250 g of o-dichlorobenzene, and additionally the previously prepared catalyst in the form of the suspension. The mixture was reacted at 80° C. at a hydrogen pressure of 0.78 MPa.-G under stirring.

After 3.5 hours, absorption of hydrogen was over. The resulting reaction solution was cooled to 70° C. and the catalyst was removed by filtration. Removal of the aqueous layer by separation afforded 345 g of an o-dichlorobenzene solution of 3-amino-9-ethylcarbazole. The analysis of the resulting solution revealed that the yield of 3-amino-9-ethylcarbazole was 97.3%.

Example 2

Into a stainless steel autoclave equipped with a stirring device, 115 g of water, 1 g of sodium hydroxide, 2.2 g of Raney nickel and 1.5 g of iron (II) sulfate were charged. After replacing the atmosphere in the vessel with hydrogen, the mixture was stirred vigorously at an ordinary temperature for one hour with adjusting the hydrogen pressure to 0.05 MPa.-G Subsequently, into the autoclave was injected a solution composed of 110 g of 3-nitro-9-ethylcarbazole (containing 98 ppm of a nitrate) and 250 g of o-dichlorobenzene. The mixture was then reacted at 80° C. at a hydrogen pressure of 0.78 MPa.-G under stirring.

After 4 hours, absorption of hydrogen was over. The resulting reaction solution was cooled to 70° C. A post-treatment was carried out in the same manner as Example 1 to afford 345 g of an o-dichlorobenzene solution of 3-amino-9-ethylcarbazole. The yield of 3-amino-9-ethylcarbazole was 95%.

Example 3

Into a flask were charged 100 g of 9-ethylcarbazole and 245 g of o-dichlorobenzene, and then nitration was carried out using nitric acid. The reaction solution was neutralized, and the oil layer separated was washed with water to provide 370 g of an o-dichlorobenzene solution of nitroethylcarbazole. The yield of 3-nitro-9-ethylcarbazoic was 90%. The resulting solution contained 110 g of 3-nitro-9-ethylcarbazole, 8 g of 1-nitro-9-ethylcarbazole. The content of the nitrate was 250 ppm.

Subsequently, into a stainless steel autoclave equipped with a stirring device were charged the whole amount of the above-obtained o-dichlorobenzene solution of nitroethylcarbazole. In addition, the whole amount of the active nickel-based catalyst prepared in the same manner as Example 1 were charged. Reduction was then carried out in the same manner as Example 1.

After 3 hours, absorption of hydrogen was over. The resulting reaction solution was subjected to a post-treatment in the same manner as Example 1 to afford 345 g of an o-dichlorobenzene solution of 3-amino-9-ethylcarbazole. The yield of 3-amino-9-ethylcarbazole was 97.1%.

Comparative Example 1

Into a stainless steel autoclave equipped with a stirring device were charged the whole amount of an o-dichlorobenzene solution of the nitroethylcarbazoles prepared in the same manner as Example 3, 115 g of water, 1 g of sodium hydroxide, 2.2 g of Raney nickel and 1.5 g of iron(II) sulfate. Then reduction was carried out in the same manner in Example 3.

After 17 hours, absorption of hydrogen was over. The resulting reaction solution was subjected to a post-treatment in the same manner as Example 3 to afford 345 g of an o-dichlorobenzene solution of 3-amino-9-ethylcarbazole. The yield of 3-amino-9-ethylcarbazole was 83%.

What is claimed is:

1. A method for constantly producing an aminocarbazole by catalytically reducing a nitrocarbazole, said method comprising:

contacting a nickel-based catalyst with an alkali and an iron compound under a hydrogen gas or inert gas atmosphere in an inert solvent to prepare a suspension solution of an active nickel-based catalyst, and thereafter reacting said nitrocarbazole with hydrogen in the presence of the suspension solution of the active nickel-based catalyst.

2. An industrial production method for constantly producing an aminocarbazole by catalytically reducing a nitrocarbazole, said method comprising:

contacting a nickel-based catalyst with an alkali and an iron compound under a hydrogen gas or inert gas atmosphere in an inert solvent to prepare a suspension solution of an active nickel-based catalyst, and thereafter reacting said nitrocarbazole with hydrogen in the presence of the suspension solution of the active nickel-based catalyst.

3. The method according to claim 2 wherein the active nickel-based catalyst is a catalyst prepared using the iron compound in the amount of from 0.1 to 0.6 times by weight based on the nickel-based catalyst in terms of metal.

4. The method according to claim 2, wherein the nitrocarbazole is a 1-nitro-9-lower alkyl-substituted carbazole and/or a 3-nitro-9-lower alkyl-substituted carbazole.

5. The method according to claim 2, wherein the alkali is selected from the group consisting of alkali metal bicarbonates, alkali metal carbonates, and alkali metal hydroxides.

6. The method according to claim 2, wherein the inert solvent is selected from the group consisting of water, lower alcohols, and mixtures thereof.

7. The method according to claim 2, wherein the amount of inert solvent is from about 5 to 100 times by weight based on the total weight of the nickel-based catalyst and the iron compound.

8. The method according to claim 2, wherein the pressure of the hydrogen gas or inert gas is from 0 to 19.6 MPa.-G (gauge pressure).

9. The method according to claim 2, wherein the temperature at which the nickel-based catalyst is contacted with the alkali and the iron compound is from about 0° to 200° C.

10. The method according to claim 1, wherein the active nickel-based catalyst is a catalyst prepared using the iron compound in the amount of from 0.1 to 0.6 times by weight based on the nickel-based catalyst in terms of metal.

11. The method according to claim 1, wherein the nitrocarbazole is a 1-nitro-9-lower alkyl-substituted carbazole and/or a 3-nitro-9-lower alkyl-substituted carbazole.

12. The method according to claim 1, wherein the alkali is selected from the group consisting of alkali metal bicarbonates, alkali metal carbonates, and alkali metal hydroxides.

13. The method according to claim 1, wherein the inert solvent is selected from the group consisting of water, lower alcohols, and mixtures thereof.

14. The method according to claim 1, wherein the amount of inert solvent is from about 5 to 100 times by weight based on the total weight of the nickel-based catalyst and the iron compound.

15. The method according to claim 1, wherein the pressure of the hydrogen gas or inert gas is from 0 to 19.6 MPa.-G (gauge pressure).

16. The method according to claim 1, wherein the temperature at which the nickel-based catalyst is contacted with the alkali and the iron compound is from about 0° to 200°.

17. A method for producing an aminocarbazole comprising:

preparing a solution of active nickel-based catalyst by contacting a nickel-based catalyst with an alkali, an iron compound, and an inert solution by stirring in the presence of a hydrogen gas or inert gas atmosphere.

18. The method of claim 17, further comprising reacting a nitrocarbazole with hydrogen in the presence of the solution of active nickel-based catalyst.

* * * * *